United States Patent [19]

Hess et al.

[11] Patent Number: 5,145,920

[45] Date of Patent: Sep. 8, 1992

[54] OLIGOMER EPOXY RESINS BASED ON CYCLOHEXYLDIPHENOL DERIVATIVES AND REACTION PRODUCTS THEREOF WITH (METH)ACRYLIC ACID AND DIISOCYANATES

[75] Inventors: Bernhard Hess, Moers; Dieter Freitag; Karsten-Josef Idel, both of Krefeld, all of Fed. Rep. of Germany

[73] Assignee: Bayer Aktiegesellschaft, Leverkusen, Fed. Rep. of Germany

[21] Appl. No.: 625,114

[22] Filed: Dec. 10, 1990

Related U.S. Application Data

[62] Division of Ser. No. 536,321, Jun. 11, 1990, Pat. No. 5,081,269.

[30] Foreign Application Priority Data

Jun. 22, 1989 [DE] Fed. Rep. of Germany ....... 3920410

[51] Int. Cl.$^5$ ............................................. C08G 59/00
[52] U.S. Cl. .................................... 525/528; 525/531; 528/73; 528/98
[58] Field of Search ................. 525/528, 531; 528/73, 528/98

[56] References Cited

U.S. PATENT DOCUMENTS

| | | | |
|---|---|---|---|
| 3,298,998 | 1/1967 | McConnell et al. | 528/97 |
| 3,410,825 | 12/1968 | Coover et al. | 528/97 |
| 5,041,521 | 8/1991 | Serini et al. | 528/194 |

*Primary Examiner*—John C. Bleutge
*Assistant Examiner*—Frederick Krass
*Attorney, Agent, or Firm*—Connolly and Hutz

[57] ABSTRACT

The invention relates to oligomer epoxy resins which are derived especially from diphenols or from diglycidyl ethers based on these phenols, oligomer epoxy resins containing oxazolidinone groups and based on the novel diglycidyl ethers and curable mixtures containing the novel oligomer epoxy resins, and the reaction products of the novel oligomer epoxy resins with unsaturated carboxylic acids, preferably in the presence of a vinyl monomer to give phenacrylate resins, and phenacrylate resins containing oxazolidinone groups and based on the novel diglycidyl ethers.

19 Claims, No Drawings

OLIGOMER EPOXY RESINS BASED ON CYCLOHEXYLDIPHENOL DERIVATIVES AND REACTION PRODUCTS THEREOF WITH (METH)ACRYLIC ACID AND DIISOCYANATES

This application is a divisional of Ser. No. 536,321 filed Jun. 11, 1990, now U.S. Pat. No. 5,081,269.

The invention relates to oligomer epoxy resins which are derived especially from diphenols or from diglycidyl ethers based on these phenols, oligomer epoxy resins containing oxazolidinone groups and based on the novel diglycidyl ethers and curable mixtures containing the novel oligomer epoxy resins, and the reaction products of the novel oligomer epoxy resins with unsaturated carboxylic acids, preferably in the presence of a vinyl monomer to give phenacrylate resins, and phenacrylate resins containing oxazolidinone groups and based on the novel diglycidyl ethers.

Cyclohex-1-ylmethylenediphenols are known, for example from British application 1 024 012. Bicyclo[2,2,1]hept-1-ylmethylenediphenols from British application 1 024 013. These compounds are employed, for example as monomer components in the preparation of polycarbonate, for example (British application 1 024 011). The preparation of glycidyl ethers of hydroxyaryl-3,4-epoxycyclohexylmethanes is known, for example from Ref. Zh. Khim., 1985, Abstract No. 19S419. The compounds prepared there have low molecular weight and consequently have a relatively low viscosity. For certain applications, for example laminates, higher oligomer compositions are advantageous.

Oligomers of this type are described, for example in European Application 278 900 based on cyclohex-1-ylmethylene-diphenols or bicyclo(2.2.1)hept-1-ylmethylenediphenol derivatives. However, products of this type are sensitive to oxidative influences (weathering) and thermal stresses due to the CH groups present between the phenol groupings.

Novel oligomer epoxy resins have been found which are not sensitive to oxidative influences, have good flow behaviour, have high glass temperatures in the cured state and can be reacted with (meth)acrylic acid to give phenacrylate resins which are characterised by a very good styrene tolerance, even in the form of phenacrylate resins containing oxazolidinone groups.

The invention relates to compounds of the formula (I) and (II)

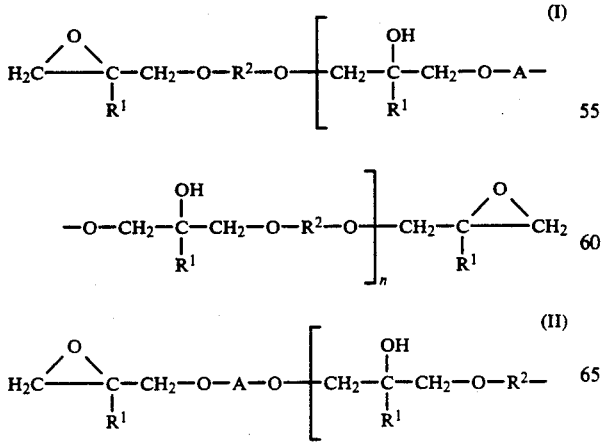

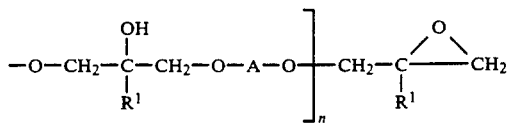

in which $R^1$ represents hydrogen, $C_1$–$C_{10}$-alkyl, preferably H, $CH_3$, $R^2$ represents $C_1$–$C_{20}$ aliphatic, $C_5$–$C_{14}$ cycloaliphatic, $C_6$–$C_{24}$ aromatic or $C_7$–$C_{30}$ araliphatic divalent radicals, n represents a number from 1 to 20, preferably 1 to 10, particularly preferably the number 1, 2, 3, 4 or 5, and A represents a radical of the formula (III)

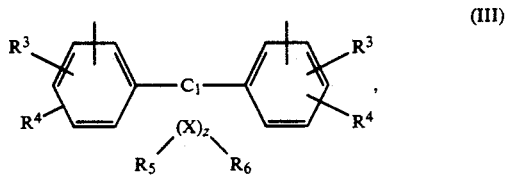

in which $R^3$ and $R^4$ independently of one another denote hydrogen, halogen, preferably chlorine, bromine, $C_1$–$C_8$-alkyl, $C_5$–$C_6$-cycloalkyl, $C_6$–$C_{10}$-aryl, preferably phenyl and $C_7$–$C_{12}$-aralkyl, preferably phenyl-$C_1$–$C_4$-alkyl, in particular benzyl, z represents the number 4, 5, 6 or 7, preferably 4 or 5, $R^5$ and $R^6$ can be selected individually for each X and independently of one another represent hydrogen, $C_1$–$C_{12}$-alkyl, methyl, ethyl is preferred, and X represents carbon.

X is particularly preferred with the proviso that, at at least one atom X, preferably at 1 or 2 atoms X, in particular at 1 atom X, $R^5$ and $R^6$ simultaneously denote $C_1$–$C_{12}$-alkyl, preferably methyl, wherein at least one X atom is not geminally dialkyl-substituted in the α-position to C1, preferably both X atoms are not geminally dialkyl-substituted in the α-position to C1, and in particular the X atom which is geminally dialkyl-substituted is in the β-position to C1.

The free bonds should preferably be in the 3-position or 4-position to the bridge C1.

Particularly preferred examples in Formula (I) and (II) contain radicals of the formulae (IV), (V) and/or (VI) as group A

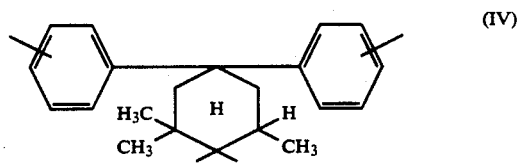

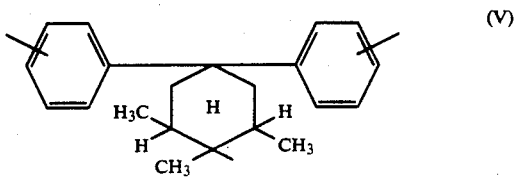

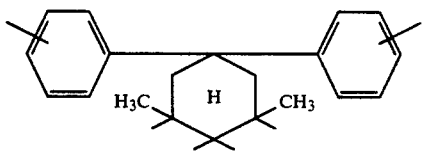

(VI)

They can be obtained in the form of the diols by condensation of hydrated isophorone or of the corresponding dialkylated cyclohexanones or trialkylated cyclohexanones with phenol in various isomers. The examples which are derived from hydrated isophorone are very particularly preferred.

If $R^2$ is derived from an aliphatic diol, we thus have straight-chain or branched-chain alkylene radicals which can be interrupted optionally by oxygen or sulphur atoms, and which can carry optional substituents (for example halogen such as Cl, Br).

Unsubstituted straight-chain $C_2$–$C_{20}$-alkylene radicals, for example ethylene, trimethylene, tetramethylene, pentamethylene, hexamethylene, haptamethylene, octamethylene, decamethylene, dodecamethylene, tetradecamethylene, hexadecamethylene, octadecamethylene, eicosamethylene are preferred, tetramethylene is particularly preferred.

The diol based on $R^2$ can also be a poly-(oxyalkylene)-glycol or a poly-(thioalkylene)-glycol. The oxygen-containing derivatives, for example poly-(ethylene)-glycol, poly-(propylene)-glycol, poly-(butylene)-glycol having 2–60 monomer units are preferred.

If $R^2$ is derived from a cycloaliphatic diol, we thus have, for example a diol with a cycloaliphatic ring having 5–7 carbon atoms which can be optionally a part of an aliphatic chain or which carries optional substituents directly on the ring. Examples of radicals of this type are preferably cyclopentylene, cyclohexylene or cycloheptylene. Cyclohexylene is particularly preferred, in particular 1,3-cyclohexylene or 1,4-cyclohexylene and hexahydroxylylene.

If $R^2$ is based on an aromatic diol, this radical is preferably derived from a mononuclear or binuclear phenol. Examples of this are 1,2-phenylene or in particular 1,3-phenylene or 1,4-phenylene and radicals of the formula (VII)

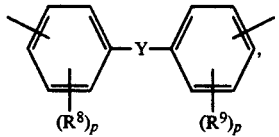

(VII)

wherein
the free bonds are preferably in 3-position or 4-position to bridge Y, and
Y is a direct C—C bond or is —$CH_2$—, —$CHCH_3$—, —$C(CH_3)_2$—, —O—, —S—, —$SO_2$— or —CO—,
p is a whole number from 0 to 4, preferably 0, 1 or 2, and
$R^8$ and $R^9$ independently of one another denote $C_1$ to $C_6$ alkyl, chlorine or bromine.

Preferred radicals $R^2$ are diphenylmethane-4,4'-diyl, diphenylether-4,4'-diyl, diphenylsulphon-4,4'-diyl and very particularly diphenyl-2,2-propylidene-4,4'-diyl. $R^2$ as an araliphatic radical is, for example xylylene.

The compounds of the formula (I) or (II) are present as a rule as a mixture of components of different chain length. The average molecular weight (number average; determined by gel permeation chromatography) is at least as large as the molecular weight of the corresponding pure monomer compound (n=1). The average value of n is preferably a number from 1 to 10 and very particularly from 1 to 5.

The preparation of the oligomer epoxides according to the formulae I or II is carried out analogously to known processes (for example the synthesis of long chain diglycidyl ethers based on bisphenol, for example according to "Epoxy Handbook" Chapters 2 to 9) by Lee and Neville.

The present invention also relates to reaction products of the compounds of the formula (II) where n=0 with diisocyanates to give oligoepoxy resins containing oxazolidinone groups according to German application 3 720 759.

Especially suitable diisocyanates are aromatic diisocyanates which have two NCO groups of different reactivity in an amount of at least ¼ of the weight of the diisocyanates, such as for example o,p-toluylenediisocyanate, diphenylmethane-2,4'-diisocyanate, 1,3-naphthylenediisocyanate alone or as a mixture with one another or as a mixture with other diisocyanates which have two NCO groups of the same reactivity, o,o-toluylenediisocyanate, 1,5-naphthylenediisocyanate. In this case the diisocyanates having NCO groups of different reactivity should account for at least ¼ of the total weight of diisocyanates.

The catalysts suitable for the process of the invention are phosphonium salts.

The process is carried out at a temperature of 140° to 180° C., preferably 150° to 170° C.

The ratio of amounts in which the bisepoxides are reacted with the diisocyanates is 1.4 to 2.5 epoxy groups for each NCO group, preferably 1.6 to 2.2 epoxy groups for each NCO group. In each case reactive epoxy groups are left over in the final product which are available for subsequent reactions or for crosslinking. The smaller the excess of epoxy groups compared to the NCO groups, the higher the molecular weight of the modified epoxy resins becomes, and the higher the melt viscosity thereof becomes.

The invention also relates to a curable mixture containing
a) at least one compound of the formula I, II or oligoepoxy resins having oxazolidinone groups,
b) an amount of an epoxy resin curing agent sufficient to cure said mixture, and
c) optionally a curing accelerator.

Suitable epoxy curing agents b) are acid, basic or catalytic curing agents. These include, for example, amines, amides, such as aliphatic, cycloaliphatic or aromatic, primary, secondary or tertiary amines, for example hexamethylenediamine, N,N-diethylpropylenediamine, bis-(4-aminocyclohexyl)-methane, 3,5,5-trimethyl-3-(aminomethyl)-cyclohexylamine ("isophoronediamine", 2,4,6-tris-(dimethylaminomethyl)-phenol, p-phenylenediamine, bis-(4-aminophenyl)-methane; polyamides, for example those of aliphatic polyamines and dimerised or trimerised unsaturated fatty acids; multivalent phenols, such as, for example resorcinol, 2,2-bis(4-hydroxyphenyl)-propane, phenol-formaldehyde resins (phenol-novolaks); boron trifluoride and its complexes with organic compounds, for example $BF_3$-ether complexes, $BF_3$-amine complexes; polybasic carboxylic acids and anhydrides thereof, for example phthalic acid anhydride, tetrahydrophthalic acid anhydride, hexahydrophthalic acid anhydride or the corresponding acids and the like.

In addition, curing accelerators c) can be used for curing; such acclerators are, for example tertiary amines, salts thereof or quaternary ammonium compounds, for example benzyldimethylamine, 2,4,6-tris(-dimethylaminomethyl)phenol, 1-methylimidazole, 2-ethyl-4-methylimidazole, 4-aminopyridine, 2,4,6-tripentylammoniumphenolate, tetramethylammoniumchloride; alkali metal alcoholates, for example sodium alcoholates of 2,4-dihydroxy-3-hydroxymethylpentane.

Curable mixtures of this type may contain suitable plasticisers, such as dibutylphthalate, dioctylphthalate or tricresylphosphate, reactive diluents, such as phenylglycidyl ether or cresylglycidyl ether, butanediolglycidyl ether, diglycidyl hexahydrophthalate, and the like.

The curable mixtures can be treated before curing in any phase with extenders, fillers and reinforcing agents, such as coal tar, bitumen, textile fibres, glass fibres, asbestos fibres, boron fibres, carbon fibres, mineral silicates, mica, quartz powder, alumunium hydroxide, bentonites, kaolin, silicic acid aerogel, metal powders, for example aluminium powder, iron powder, with pigments, dyestuffs, such as soot, oxide colours, titanium dioxide, and the like. Other conventional additives, for example flame retardants, such as antimony trioxide, thixotroping agents, flow control agents, such as silicones, waxes or stearates (some of which are also used as mould release agents) can also be added to the curable mixtures.

The preparation of the curable mixtures of the invention can be carried out in conventional manner with the aid of known mixing apparatus (stirrers, kneaders, rollers and the like).

The curable epoxy resin mixtures of the invention are particularly used in all fields of surface protection, electronics, laminating processes and in building and construction. They can be used in the formulation adapted in each case to the specific purpose, in the unfilled or filled state, as paints, coatings, such as sinter powder coatings, as compression moulding compounds, dipping resins, casting resins, injection moulding formulations, impregnating resins and adhesives, as tooling resins, laminating resins, sealing and mastic compounds, floor covering compounds and binders for mineral machines.

They are preferably used as sinter powder coatings, impregnating and laminating resins, in particular as impregnating and laminating resins.

The curing of the copolymers containing glycidyl groups according to the invention is preferably carried out in the temperature range from 50° C. to 300° C., preferably from 80° to 250° C.

The curing can also be carried out in known manner in two or more stages, wherein the first curing stage is carried out at low temperature and the subsequent curing at higher temperature.

If desired, the curing can also be carried out in 2 stages such that the curing reaction is initially terminated prematurely or the first stage is carried out at slightly increased temperature, wherein a curable precondensate (so-called "B stage") which can still be melted and/or dissolved, is obtained from the epoxy component a), curing agent b) and optionally present accelerator c). A precondensate of this type can serve, for example to prepare "prepegs", compression moulding compounds or sinter powders.

The present invention also relates to reaction products of the compounds of the formulae (I) and (II)-formula (II) also when n=0-and reaction products of the oligoepoxy resins containing oxazolidinone groups described and unsaturated carboxylic acids, preferably acrylic or methacrylic acid in the presence of a catalyst, preferably in the presence of a vinyl monomer according to German application 3 723 196.

Suitable unsaturated carboxylic acids are ethylenically unsaturated carboxylic acids, for example methacrylic acid, acrylic acid, cinnamic acid and half esters of a dicarboxylic acid and an unsaturated hydroxyalkylcarboxylate. Acrylic acid and methacrylic acid is preferred.

The epoxy resins and unsaturated carboxylic acids are preferably employed in approximately stoichiometric ratios, that is approximately one equivalent of carboxylic acids is employed per epoxy equivalent of the resin.

Suitable catalysts are quaternary ammonium salts, such as halides, acetates or formates.

Catalysts of this type are described for example in British application 1 364 804. Tetraethylammoniumbromide, tetraethylammoniumchloride, tetrabutylammoniumbromide, tetrabutylammoniumchloride, triethylbenzylammoniumchloride and triethylbenzylammoniumbromide are preferred.

Suitable catalysts are phosphonium halides.

Suitable phosphonium salts are described, for example in European application 99 334. Examples of particularly preferred phosphonium compounds are tetrabutylphosphoniumbromide, tetrabutylphosphoniumchloride, triphenylbenzylphosphoniumchloride and triphenylbenzylphosphoniumbromide.

Vinyl monomers which can be employed are those which are inert to epoxy groups under the reaction conditions, for example styrene, ring-chlorinated, ring-alkylated or ring-alkenylated styrenes, wherein the alkyl groups may contain 1 to 4 C atoms, such as vinyl toluene, divinylbenzene, -methylstyrene, tert.-butylstyrene, chlorinated styrenes, vinyl esters of carboxylic acids having 2 to 6 C atoms, preferably vinyl acetate, vinyl pyridine, vinyl naphthalene, vinyl cyclohexane, acrylates and methacrylates without functional groups, allyl compounds, such as allyl benzene and allyl esters, such as allyl acetate, diallyl phthalates, diallyl isophthalates, allyl carbonates, triallylphosphonate, triallylcyanurate. Styrene is preferred.

The phenacrylate resins described may also be bonded to acid groups by re-acidifying with acid anhydrides to give acid half esters. The resins can then be thickened by means of these groups, for example with MgO (for example when processing to form so-called resin mats.

To re-acidify (reaction with acid anhydrides to give acid half esters) the phenacrylate resin solution in vinyl monomers formed, suitable acid anhydrides are preferably the anhydrides of succinic acid, phthalic acid, tetrahydrophthalic acid, methyltetrahydrophthalic acid, hexahydrophthalic acid, methylhexahydrophthalic acid, endomethylenetetrahydrophthalic acid, endomethylenehexahydrophthalic acid, hexachloroendomethylenetetrahydrophthalic acid, and the like; the anhydrides of (methyl)tetrahydrophthalic acid or (methyl)hexahydrophthalic acid are preferred.

The amount of acid anhydride should be such that an acid number of 15 to 80, preferably 30 to 60 can be determined (for example calculated or titrated) for the re-acidified phenacrylate resin.

The invention also relates to the use of the curable compounds, in particular of the reaction products of the compounds of the formulae I, II containing acrylate or methacrylate groups, or of the oligoepoxy resins containing oxazolidinone groups preferably in vinyl monomer solution, such as styrene, alkylated or halogenated styrenes for the preparation of coatings, casting resins, mastic compounds, compression moulding compounds, fibre-containing laminates and adhesives.

EXAMPLES

Meaning of Abbrevations

X20: Bisphenol-A-bisglycidylether, technical, epoxy equivalent weight: 186
BPA: Bisphenol A
HIP: Bis(4-hydroxyphenyl)-3,3,5-trimethylcyclohexane)[1]
HIP-(EP): Bis(4-hydroxyphenyl)-3,3,5-trimethylcyclohexane (bisglycidylether); epoxy equivalent weight: 235
MDI-M: Mixture of 59% 4,4'-diphenylmethanediisocyanate, 34% 2,4'diphenylmethanediisocyanate and 6% 2,2'-diphenylmethanediisocyanate
Cu solution: Copper naphthenate, 10% strength solution in styrene, containing 1% copper metal.
Catalyst A: Tetrabutylphosphoniumbromide
Catalyst B: Triethylbenzylammoniumchloride

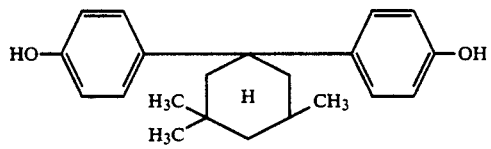

1)

The amounts given in the tables are parts by weight.

PREPARATION OF EXAMPLES 1 AND 2 AND COMPARATIVE EXAMPLES

The amounts of epoxy resin listed in Table I and the catalyst B are weighed out in a stirring flask and heated under nitrogen to the reaction temperature given in Table I. HIP or BPA is added in the course of about 30 minutes in portions with stirring at this temperature and the temperature is maintained for 3 hours. After this time the epoxy value is reduced to the calculated value and phenolic OH is no longer present. The epoxy equivalent weights and the melting range of the oligoepoxy resins are also listed in the table. Furthermore, the glass temperature of the cured products is given in Table I after the conventional heat curing with hexahydrophthalic acid anhydride corresponding to the epoxy equivalent weights.

The table clearly shows the higher glass temperatures of the examples compared to the comparative examples.

TABLE I

| Example: Comparative example | 1 | 1a | 2 | 2a | 1b |
|---|---|---|---|---|---|
| X20 | 100 | 100 | — | — | 100 |
| HIP-EP | — | — | 100 | 100 | — |
| HIP | 41.0 | — | 32.6 | — | — |
| BPA | — | — | — | — | 30 |
| Catalyst B | 0.05 | — | 0.05 | — | 0.05 |

TABLE I-continued

| Example: Comparative example | 1 | 1a | 2 | 2a | 1b |
|---|---|---|---|---|---|
| Reaction temperature (°C.) | 150 | — | 185 | — | 130 |
| Epoxy equivalent weight | 514 | 186 | 675 | 232 | 500 |
| Melting range [°C.] | 90 | liquid | 130 | 40/50 | 70 |
| Glass temperature (°C.) | 200 | 125 | 218 | 150 | 115 |

The amounts given in the table are parts by weight.

EXAMPLE 3 AND COMPARATIVE EXAMPLE 3a (Oligoepoxy resin containing oxazolidinone groups)

The amounts of bis-epoxy resins and catalyst A listed in Table II in each case are weighed into a flask fitted with stirrer and gas inlet tube and heated under nitrogen at 160° C. The diisocyanate (MDI-M) is added dropwise to the melt quickly so that a temperature of 170° C. is not exceeded; this can be controlled by switching off the heat or by cooling. After adding the diisocyanate, the mixture is stirred at 160° C. until the epoxy value calculated is reached and reactive NCO is no longer detectable. The finished melt is removed while hot and allowed to solidify.

TABLE II

| Example/Comparison | 3 | 3a |
|---|---|---|
| X20 | — | 224.5 |
| HIP-EP | 289 | — |
| Catalyst A | 0.74 | 0.22 |
| MDI-M | 80 | 75.5 |
| Reaction time (hours) | 1 | 3 |
| Epoxy equivalent: NCO | 2:1 | 2:1 |
| % NCO | 0 | 0 |
| Epoxy equivalent weight: | 595 | 503 |
| Melting range (°C.) | 134/140 | 88/94 |

Heat curing of Examples 3 and 3a in combination with a liquid bisphenol-A-bisglycidylether:

TABLE III

| Composition of the mixtures: | |
|---|---|
| Bisphenol-A-bisglycidylether, technical | 75 parts by weight |
| Oxazolidinone epoxy resin Example 3 and 3a | 25 parts by weight |
| Hexahydrophthalic acid anhydride | 70 parts by weight |
| Dimethylbenzylamine | 1.7 parts by weight |
| Glass temperature with Example: | 3 | 3a |
| | 145° | 110° C. |

In each case 25 g of oxazolidinone epoxy resin of Example 3 or 3a are dissolved in 75 g of bisphenol-A-bisglycidylether, technical quality, at 100° to 110° C., and added to the solution of 70 g of hexahydrophthalic acid anhydride. The melt is cooled to room temperature, stirred into 1.7 g of dimethylbenzylamine, evacuated and then poured between two glass plates 4 mm apart. The plates are partially cured for 4 hours at 80° C., then cured to completion for 16 hours at 120° C., and then removed from the plates. The cured material is cut into standard size rods and measured mechanically. It has the values listed in Table III.

In comparison to Example 3a, Example 3 clearly shows higher thermal dimensional stability.

The following examples and comparative examples describe reaction products of oligoepoxy resins with methacrylic acid in vinyl monomer solution.

PREPARATION OF EXAMPLES 4 TO 7 AND COMPARATIVE EXAMPLE

The parts by weight of Examples 1 to 3, the composition of which is shown specially in tabular form to be seen clearly, listed in each case in Table IV are weighed into a flask fitted with stirrer and gas inlet tube and dissolved in styrene and optionally vinyl toluene which contains the amounts of inhibitors and Cu solution listed. The corresponding amount of catalyst B is added to the solution and heated at 110° C. with stirring and passage of air. The methacrylic acid is added dropwise in the course of approximately 15 minutes and the solution is maintained at 110° C. until the methacrylic acid content is reduced to <1%, relative to all components without styrene.

The examples and comparative examples of Table IV show the thermal dimensional stability listed in the table after heat curing with 1 wt. % of tert.-butylperbenzoate at 120° C. and subsequent tempering at 120° C. for 15 hours. It is significantly higher than that of the comparative example.

TABLE IV

| Example | 4a | 4 | 5 | 6 | 7 |
|---|---|---|---|---|---|
| X20 | 100 | 100 | — | — | — |
| HIP-EP | — | — | 100 | 100 | 100 |
| BPA | 30 | — | — | — | — |
| HIP | — | 41 | 32.6 | — | — |
| MDI-M | — | — | — | 27.7 | — |
| Example resin | 1b | 1 | 2 | 3 | — |
| Catalyst B | 0.75 | 0.75 | 0.75 | 0.75 | 0.75 |
| Styrene | 113.3 | 134 | 123.3 | 56.6 | 88.9 |
| Vinyltoluene | — | — | — | 22.7 | — |
| Toluhydroquinone | 0.038 | 0.038 | 0.038 | 0.038 | 0.038 |
| Di-tert.-butylquinone | 0.038 | 0.038 | 0.038 | 0.038 | 0.038 |
| Cu solution | 0.38 | 0.38 | 0.38 | 0.38 | 0.38 |
| Methacrylic acid | 22 | 22.8 | 18.1 | 20.4 | 33.4 |
| Viscosity at 20° C. (mPas) | 1250 | 710 | 1000 | 31,400 | 117 |
| Martens measurement | 100 | 107 | 116 | 125 | 134 |
| Glass temperature (°C.) | 119 | 125 | 129 | 136 | 150 |

We claim:

1. Curable mixtures comprising
a) at least one compound of the formulae (I) or (II)

$$H_2C\overset{O}{\underset{}{\diagup\!\!\!\diagdown}}\underset{R^1}{C}-CH_2-O-R^2-O-\left[CH_2-\underset{R^1}{\overset{OH}{C}}-CH_2-O-A-\right.$$ (I)

$$\left.-O-CH_2-\underset{R^1}{\overset{OH}{C}}-CH_2-O-R^2-O\right]_n-CH_2-\underset{R^1}{\overset{O}{\underset{}{C}}}\overset{}{\diagdown}CH_2$$

$$H_2C\overset{O}{\underset{}{\diagup\!\!\!\diagdown}}\underset{R^1}{C}-CH_2-O-A-O-\left[CH_2-\underset{R^1}{\overset{OH}{C}}-CH_2-O-R^2-\right.$$ (II)

$$\left.-O-CH_2-\underset{R^1}{\overset{OH}{C}}-CH_2-O-A-O\right]_n-CH_2-\underset{R^1}{\overset{O}{\underset{}{C}}}\overset{}{\diagdown}CH_2$$

in which $R^1$ represents hydrogen or $C_1$–$C_{10}$-alkyl, $R^2$ represents $C_1$–$C_{20}$-aliphatic, $C_5$–$C_{14}$-cycloaliphatic, $C_6$–$C_{24}$-aromatic or $C_7$–$C_{30}$ araliphatic divalent radicals with the proviso that $R^2$ is not the same as A, n represents a number from 1 to 20, and A represents a radical of the formula (III)

(III)

in which $R^3$ and $R^4$ independently of one another denote hydrogen, halogen, $C_1$–$C_8$-alkyl, $C_5$–$C_6$-cycloalkyl, $C_6$–$C_{10}$-aryl, or $C_7$–$C_{12}$-aralkyl, z represents the number 4, 5, 6 or 7, $R^5$ and $R^6$ can be selected individually for each X and independently of one another represent methyl or ethyl and X represents carbon, b) an amount of an epoxy resin curing agent sufficient to cure the mixture, and c) optionally a curing accelerator.

2. Curable mixture according to claim 1 wherein $R^1$ represents H or $CH_3$.

3. Curable mixture according to claim 1 wherein n represents a number from 1 to 10.

4. Curable mixture according to claim 3 wherein n represents a number from 1 to 5.

5. Curable mixture according to claim 1 wherein $R^3$ and $R^4$ independently of one another denote chlorine or bromine.

6. Curable mixture according to claim 1 wherein $R^3$ and $R^4$ independently of one another denote phenyl.

7. Curable mixture according to claim 1 wherein $R^3$ and $R^4$ independently of one another denote benzyl.

8. Curable mixture according to claim 1 wherein $R^3$ and $R^4$ independently of one another denote phenyl-$C_1$–$C_4$-alkyl.

9. Curable mixture according to claim 1 wherein z represents 4 or 5.

10. Curable mixture comprising
a) the reaction product of diisocyanates with at least one compound of the formulae (I) or (II)

$$H_2C\overset{O}{\underset{}{\diagup\!\!\!\diagdown}}\underset{R^1}{C}-CH_2-O-R^2-O-\left[CH_2-\underset{R^1}{\overset{OH}{C}}-CH_2-O-A-\right.$$ (I)

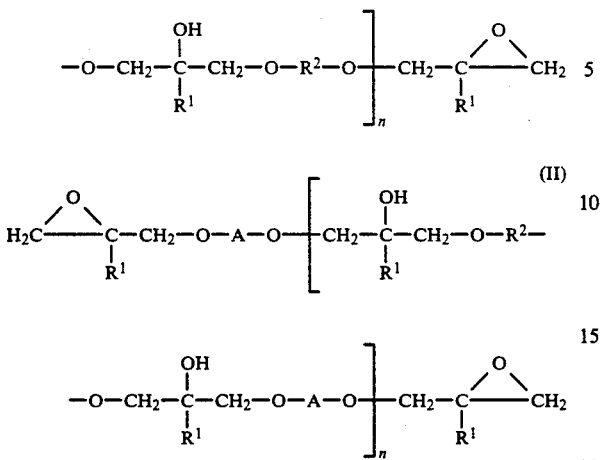

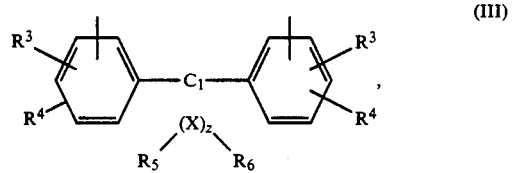

in which
R¹ represents hydrogen or $C_1$–$C_{10}$-alkyl,
R² represents $C_1$–$C_{20}$-aliphatic, $C_5$–$C_{14}$-cycloaliphatic, $C_6$–$C_{24}$-aromatic or $C_7$–$C_{30}$ araliphatic divalent radicals with the proviso that R² is not the same as A,
n represents a number from 1 to 20, and
A represents a radical of the formula (III)

(III)

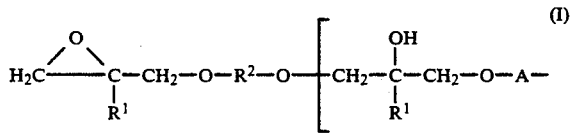

in which
R³ and R⁴ independently of one another denote hydrogen, halogen, $C_1$–$C_8$-alkyl, $C_5$–$C_6$-cycloalkyl, $C_6$–$C_{10}$-aryl, or $C_7$–$C_{12}$-aralkyl,
z represents the number 4, 5, 6 or 7,
R⁵ and R⁶ can be selected individually for each X and independently of one another represent methyl or ethyl and
X represents carbon, b) an amount of an epoxy resin curing agent sufficient to cure the mixture, and c) optionally a curing accelerator.

11. Oligo-epoxide resins containing oxazolidone groups wherein the resins are the reaction products of diisocyanates with compounds of the formulae (I) or (II)

(I)

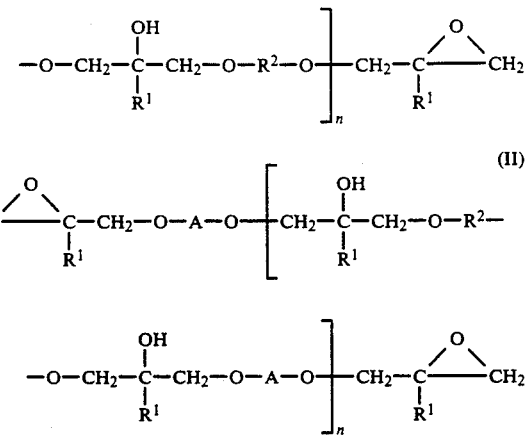

(II)

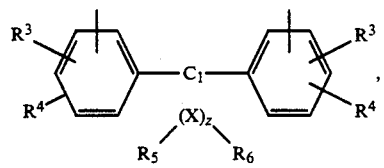

in which
R¹ represents hydrogen or $C_1$–$C_{10}$-alkyl,
R² represents $C_1$–$C_{20}$-aliphatic, $C_5$–$C_{14}$-cycloaliphatic, $C_6$–$C_{24}$-aromatic or $C_7$–$C_{30}$ araliphatic divalent radicals with the proviso that R² is not the same as A,
n represents a number from 1 to 20, and
A represents a radical of the formula (III)

(III)

in which
R³ and R⁴ independently of one another denote hydrogen, halogen, $C_1$–$C_8$-alkyl, $C_5$–$C_6$-cycloalkyl, $C_6$–$C_{10}$-aryl, or $C_7$–$C_{12}$-aralkyl,
z represents the number 4, 5, 6 or 7,
R⁵ and R⁶ can be selected individually for each X and independently of one another represent methyl or ethyl and
X represents carbon.

12. Oligo-epoxide resins according to claim 11 wherein R¹ represents H or $CH_3$.

13. Oligo-epoxide resins according to claim 11 wherein n represents a number from 1 to 10.

14. Oligo-epoxide resins according to claim 13 wherein n represents a number from 1 to 5.

15. Oligo-epoxide resins according to claim 4 wherein R³ and R⁴ independently of one another denote chlorine or bromine.

16. Oligo-epoxide resins according to claim 11 wherein R³ and R⁴ independently of one another denote phenyl.

17. Oligo-epoxide resins according to claim 11 wherein R³ and R⁴ independently of one another denote phenyl-$C_1$–$C_4$-alkyl.

18. Oligo-epoxide resins according to claim 17 wherein R³ and R⁴ independently of one another denote benzyl.

19. Oligo-epoxide resins according to claim 11 wherein z represents 4 or 5.

* * * * *